(12) United States Patent
Ballard et al.

(10) Patent No.: US 9,005,645 B2
(45) Date of Patent: *Apr. 14, 2015

(54) LIQUID TERMITICIDE COMPOSITIONS OF PYRETHROIDS AND NEONICITINOIDS

(75) Inventors: James B. Ballard, Medford, NJ (US); Cristi L. Palmer, Hightstown, NJ (US); Kim Watson, Indian Harbour Beach, FL (US)

(73) Assignee: FMC Corporation, Philadelphia, PA (US)

( * ) Notice: Subject to any disclaimer, the term of this patent is extended or adjusted under 35 U.S.C. 154(b) by 574 days.

This patent is subject to a terminal disclaimer.

(21) Appl. No.: 13/353,675

(22) Filed: Jan. 19, 2012

(65) Prior Publication Data

US 2012/0122856 A1 May 17, 2012

Related U.S. Application Data

(62) Division of application No. 10/593,619, filed as application No. PCT/US2005/009459 on Mar. 22, 2005, now Pat. No. 8,133,499.

(60) Provisional application No. 60/556,229, filed on Mar. 25, 2004.

(51) Int. Cl.
- *A01N 25/00* (2006.01)
- *A01N 25/32* (2006.01)
- *A01N 53/00* (2006.01)

(52) U.S. Cl.
CPC ...................................... *A01N 53/00* (2013.01)

(58) Field of Classification Search
None
See application file for complete search history.

(56) References Cited

U.S. PATENT DOCUMENTS

| | | | |
|---|---|---|---|
| 5,747,519 A * | 5/1998 | Kodama et al. | 514/407 |
| 8,092,816 B2 * | 1/2012 | Richman et al. | 424/405 |
| 2005/0221028 A1 * | 10/2005 | Westcott et al. | 428/34.1 |

FOREIGN PATENT DOCUMENTS

CA 2474086 A1 * 8/2003

* cited by examiner

*Primary Examiner* — Carlos Azpuru
*Assistant Examiner* — Casey Hagopian
(74) *Attorney, Agent, or Firm* — FMC Corporation

(57) ABSTRACT

The present invention relates to liquid termiticide compositions comprising a pyrethroid and a neonicotinoid selected from the group consisting of imidacloprid, nithiazine, thiamethoxam, dinotefuran, nitenpyram, thiacloprid and clothianadin, these compositions result in an increase in termite mortality at low application rates and a continuous chemical bather of a termiticide in soil surrounding and beneath a structure in a locus where termites are suspected or known to exist.

4 Claims, No Drawings

LIQUID TERMITICIDE COMPOSITIONS OF PYRETHROIDS AND NEONICITINOIDS

This application claims the benefit of U.S. Provisional Application No. 60/556,229, filed Mar. 25, 2004.

FIELD OF THE INVENTION

The present invention relates generally to pesticidal compositions. In particular, it pertains to compositions of liquid termiticides useful for control of soil-borne termites.

BACKGROUND OF THE INVENTION

Termites are undisputedly the most destructive of all structural insects. Termites are estimated to cause 1.5 billion dollars of damage to structures annually, and an additional one billion dollars is spent on treatment. Depending on the type of termite, a colony can cover as much as 22,000 square feet. These industrious insects work 24 hours a day, gradually eating wood and any other cellulose containing material in their environment. Since they remain hidden within the wood in which they are feeding, in mud tubes, or in the soil, they typically wreak havoc undetected. There are two types of termites, described as i) dry wood termites, and ii) subterranean termites. Of these two types, the subterranean termites usually live in the soil (i.e., soil-borne), from which they build mud tubes to structural wood where they then feed.

Control of soil-borne termites can be accomplished by strategic application of a termiticide to the soil where there is a termite infestation, to provide a continuous chemical bather in soil surrounding and beneath a structure. However, the final distribution of a liquid termiticide in soil is the result of a series of variables: soil moisture, soil type, solubility of the active ingredient in water, formulation type, and application variables such as volume applied, pressure and nozzle type. The preferred method for control of soil-borne termites is by the application of a termiticide directly to the surface of soil, thereby creating a chemical barrier in the soil when the termiticide leaches into the soil. Termiticides having potential utility in application directly to the surface of soil are applied in the form of a liquid termiticide. A "liquid termiticide" is defined as a composition containing at least one termiticide where the composition is dispensed in an aqueous medium prior to its application to a locus where termite control is needed.

There is a two-fold problem in the art of formulating a liquid termiticide for soil-borne termite treatment. The first problem arises when a liquid termiticide containing a relatively water-insoluble, soil-binding termiticide is applied to the soil there may be gaps, or thinly treated areas, in the desired continuous chemical barrier caused by the immobility of the termiticide in the soil. Termites, therefore, can gain access to food sources/structures through these gaps and thinly treated areas in the chemical barrier. The second problem is that previously available liquid termiticides have relatively low termite mortality rates at low application rates.

Hence, it would be advantageous to provide a liquid termiticide composition for soil treatment that affords a continuous chemical barrier and increased termite mortality at low application rates.

SUMMARY OF THE INVENTION

It has now been unexpectedly found that a composition comprising a pyrethroid, such as bifenthin, and a neonicitinoid, such as imidacloprid, clothianidin, or thiamethoxin, provides a continuous chemical barrier and increased termite mortality at low application rates. The neonicitinoid provides good soil mobility for a very effective continuous chemical barrier. The combination of the pyrethroid and neonicitinoid provide for an unexpected increase in termite mortality at low application rates. Specifically, the present invention is a liquid termiticide composition comprising a pyrethroid and a neonicotinoid selected from the group consisting of imidacloprid, nithiazine, thiamethoxam, dinotefuran, nitenpyram, thiacloprid and clothianadin. Other aspects of the present invention will also be apparent.

DETAILED DESCRIPTION OF THE INVENTION

It has now been unexpectedly found that a liquid termiticide composition comprising a pyrethroid and a neonicotinoid selected from the group consisting of imidacloprid, nithiazine, thiamethoxam, dinotefuran, nitenpyram, thiacloprid and clothianadin. Preferably, the pyrethroid is selected from the group consisting of bifenthrin, cypermethrin, zeta cypermethrin, lambdacyhalothrin, betacyhalothrin, alphacypermethrin, tralomethrin, deltamethrin, cyfluthrin, beta-cyfluthrin, esfenvalerate, fluvalinate, etofenprox and permethrin. More preferably, the pyrethroid is bifenthrin.

A preferred composition is a mixture of bifenthrin and imidacloprid. The bifenthrin can be present in an amount of from 0.0005% by weight to 0.50% by weight of all components in the composition. The imidicloprid can be present in an amount of from 0.0005% by weight to 0.50% by weight of all components in the composition.

Another preferred composition is a mixture of bifenthrin and clothianadin. The bifenthrin can be present in an amount of from 0.0005% by weight to 0.50% by weight of all components in the composition. The clothianadin can be present in an amount of from 0.0005% by weight to 0.50% by weight of all components in the composition.

Yet another preferred composition is a mixture of bifenthrin and thiamethoxam. The bifenthrin can be present in an amount of from 0.0005% by weight to 0.50% by weight of all components in the composition. The thiamethoxam can be present in an amount of from 0.0005% by weight to 0.50% by weight of all components in the composition.

Another embodiment of the present invention comprises a method for controlling termites comprising applying a termiticidally effective amount of a composition to a locus where termite control is needed or expected to be needed. The locus can be selected from a termite-infested structure, a structure that is expected to be termite-infested, or a location adjacent to said structures.

A liquid termiticide is any composition containing a termiticide where the composition is dispensed in an aqueous medium prior to its application to a locus where termite control is needed. That is to say, a liquid termiticide is made up of 1) a termiticide, 2) an aqueous medium and 3) other additives conventionally employed in termiticidal formulations (e.g. surfactants, wetting agents, freeze/thaw agents). All compositions of termiticides that are or can be dispensed in an aqueous medium prior to application are, therefore, within the scope of the present invention (e.g. Micro-emulsions, Suspension concentrates, Emulsifiable concentrates, Wettable powders, Water dispersible granules, Capsule suspensions, Emulsifiable granules or combinations thereof).

The compositions of the present invention may be derived from commercially available formulations of termiticides. For example, bifenthrin, sold by FMC Corporation under the names and trademarks of TALSTAR® GC FLOWABLE INSECTICIDE/MITICIDE, TALSTAR® TERMITICIDE/

INSECTICIDE, or TALSTARONE® MULTI-INSECTICIDE, to name a few, find utility in the present invention. Using methods known to one skilled in the art, the above-mentioned formulations of termiticides can be dispersed in an aqueous medium to provide a composition containing a termiticidally effective amount of a termiticide.

The following examples further illustrate the present invention, but, of course, should not be construed as in any way limiting its scope. The examples set forth certain biological data illustrating the efficacy of the compositions of the present invention in controlling termites. Unless otherwise indicated, all parts, percentages, and the like are by weight of all components of the composition.

Example 1

Test to Determine Termite Mortality by Applications of Combinations of Bifenthrin and Imidacloprid The compositions of the present invention were tested for termiticide activity in the following manner:
Test compositions made up of TALSTAR® TERMITICIDE/INSECTICIDE and a wettable powder of imidacloprid in distilled water were prepared that provided appropriate rates of application of combinations of bifenthrin and imidacloprid, as well as bifenthrin and imidacloprid alone.

Glass tubing, 13 mm in diameter, was then cut into 20 cm sections in sufficient quantity to conduct the test. Each 20 mm section of tubing was marked at 5 cm, 8 cm, and 18 cm distances from one end of the tube designated as the bottom. Each section of tubing was packed with a sandy soil (3% wt/wt moisture content) by first placing a section of a 1 cm diameter wooden dowel into the bottom of the glass tube up to the 8 cm marking, then introducing approximately 2 cm of soil into the other end of the tube designated as the top. The soil was then gently packed into the tube from the top using a second section of the 1 cm diameter wooden dowel. The process was repeated using 2 cm aliquots of soil until the soil level was adjacent to the 18 cm marking, thereby providing a column of soil 10 cm in height. An agar plug, which was formed in a section of the 13 mm diameter glass tubing of the type used to conduct these tests, was cut into 3 cm sections. A 3 cm section of agar was then gently pushed into the bottom of each tube containing the soil until the agar plug firmly touched the soil at the 8 cm marking, thereby creating a 5 cm void in the bottom of each section of tubing. Following placement of the agar plugs in each section of tubing; two sections of applicator sticks cut in 6 cm lengths were inserted into the bottom end of each tube thereby forcing about 1 cm of each stick into the agar plug to hold the agar plug in place. Plastic caps, with an inside diameter of 13 mm and holes drilled in their centers, were placed on the bottom ends of each of the sections of tubing. A sharpened applicator stick was then inserted into the hole in each plastic cap through the agar plug to the intersection of the agar plug and the soil. The applicator stick was then gently removed in a rotating manner to provide a means for a free flow of liquid through the soil. Each section of tubing was then stood upright, and 0.5 mL aliquots of each suspension of bifenthrin, imidacloprid or combinations thereof, as prepared above, were pipetted onto the top of the soil. Upon application of the test suspensions the top of each section of tubing was covered with a small piece of aluminum foil. The tubes were then allowed to stand for about 20 hours to allow movement of the termiticide(s) downward into the soil. After this time a plastic cap of 13 mm inside diameter was placed on the top of each section of tubing. The plastic caps with the holes drilled in their centers were removed from the bottom of each section of tubing, and a piece of 0.5 cm×4 cm filter paper was then placed between the two sections of applicator sticks. Fifty termite (*Reticulitermes flavipes*) workers were then inserted into the 5 cm void in the bottom of each section of tubing. New plastic caps without holes drilled in their centers were placed on the bottom of each section of tubing. The sections of tubing were then stored in an upright position, with the termites located below the soil. Termite mortality was measured at 1 hour, 2 hours, 1 day, 2 days and 7 days after treatment. The following results were recorded:

TABLE 1

Control of Termites by Application of Combinations of Bifenthrin and Imidacloprid

| Treatment | Rate of Appln. (PPM) | Rate of Appln. (% by weight) | Mortality Rate @ 1 Hour (%) | Mortality Rate @ 2 Hours (%) | Mortality Rate @ 1 Day (%) | Mortality Rate @ 2 Days (%) | Mortality Rate @ 7 Days (%) |
|---|---|---|---|---|---|---|---|
| A | 10 | 0.001 | 0 | 0 | 13 | 24 | 95 |
|   | 50 | 0.005 | 0 | 0 | 21 | 78 | 100 |
| B | 100 | 0.01 | 0 | 0 | 0 | 4 | 100 |
|   | 200 | 0.02 | 0 | 0 | 1 | 6 | 100 |
| A + B | 10/100 | 0.001/0.01 | 0 | 3 | 29 | 76 | 100 |
|   | 10/200 | 0.001/0.02 | 3 | 3 | 34 | 68 | 100 |
|   | 50/100 | 0.005/0.01 | 0 | 0 | 20 | 80 | 100 |
|   | 50/200 | 0.005/0.02 | 0 | 0 | 28 | 75 | 100 |
| Untreated | 0 | 0 | 0 | 0 | 0 | 0 | 5 |

A is bifenthrin
B is imidacloprid

Example 2

Test to Determine Termite Mortality by Applications of Combinations of Bifenthrin and Clothianadin The compositions of the present invention were tested for termiticide activity in the following manner:
Test compositions made up of TALSTAR® TERMITICIDE/INSECTICIDE and a wettable powder of clothianadin in distilled water were prepared that provided appropriate rates of application of combinations of bifenthrin and clothianadin, as well as bifenthrin and clothianadin alone.

Glass tubing, 13 mm in diameter, was then cut into 20 cm sections in sufficient quantity to conduct the test. Each 20 mm section of tubing was marked at 5 cm, 8 cm, and 18 cm distances from one end of the tube designated as the bottom. Each section of tubing was packed with a sandy soil (3% wt/wt moisture content) by first placing a section of a 1 cm diameter wooden dowel into the bottom of the glass tube up to the 8 cm marking, then introducing approximately 2 cm of soil into the other end of the tube designated as the top. The soil was then gently packed into the tube from the top using a second section of the 1 cm diameter wooden dowel. The process was repeated using 2 cm aliquots of soil until the soil level was adjacent to the 18 cm marking, thereby providing a column of soil 10 cm in height. An agar plug, which was formed in a section of the 13 mm diameter glass tubing of the type used to conduct these tests, was cut into 3 cm sections. A 3 cm section of agar was then gently pushed into the bottom of each tube containing the soil until the agar plug firmly touched the soil at the 8 cm marking, thereby creating a 5 cm void in the bottom of each section of tubing. Following placement of the agar plugs in each section of tubing; two sections of applicator sticks cut in 6 cm lengths were inserted into the bottom end of each tube thereby forcing about 1 cm of each stick into the agar plug to hold the agar plug in place. Plastic caps, with an inside diameter of 13 mm and holes drilled in their centers, were placed on the bottom ends of each of the sections of tubing. A sharpened applicator stick was then inserted into the hole in each plastic cap through the agar plug to the intersection of the agar plug and the soil. The applicator stick was then gently removed in a rotating manner to provide a means for a free flow of liquid through the soil. Each section of tubing was then stood upright, and 0.5 mL aliquots of each suspension of bifenthrin, clothianidin or combinations thereof, as prepared above, were pipetted onto the top of the soil. Upon application of the test suspensions the top of each section of tubing was covered with a small piece of aluminum foil. The tubes were then allowed to stand for about 20 hours to allow movement of the termiticide(s) downward into the soil. After this time a plastic cap of 13 mm inside diameter was placed on the top of each section of tubing. The plastic caps with the holes drilled in their centers were removed from the bottom of each section of tubing, and a piece of 0.5 cm×4 cm filter paper was then placed between the two sections of applicator sticks. Fifty termite (*Reticulitermes flavipes*) workers were then inserted into the 5 cm void in the bottom of each section of tubing. New plastic caps without holes drilled in their centers were placed on the bottom of each section of tubing. The sections of tubing were then stored in an upright position, with the termites located below the soil. Termite mortality was measured at 1 hour, 2 hours, 1 day, 2 days and 7 days after treatment. The following results were recorded:

TABLE 2

Control of Termites by Application of Combinations of Bifenthrin and Clothianidin

| Treatment | Rate of Appln. (PPM) | Rate of Appln. (% by weight) | Mortality Rate @ 1 Hour (%) | Mortality Rate @ 2 Hours (%) | Mortality Rate @ 1 Day (%) | Mortality Rate @ 2 Days (%) | Mortality Rate @ 7 Days (%) |
|---|---|---|---|---|---|---|---|
| A | 10 | 0.001 | 0 | 0 | 13 | 24 | 95 |
|   | 50 | 0.005 | 0 | 0 | 21 | 78 | 100 |
| B | 100 | 0.01 | 0 | 0 | 0 | 23 | 100 |
|   | 200 | 0.02 | 0 | 0 | 1 | 11 | 100 |
| A + B | 10/100 | 0.001/0.01 | 0 | 0 | 20 | 51 | 100 |
|   | 10/200 | 0.001/0.02 | 0 | 0 | 26 | 76 | 100 |
|   | 50/100 | 0.005/0.01 | 0 | 0 | 21 | 70 | 100 |
|   | 50/200 | 0.005/0.02 | 0 | 0 | 20 | 81 | 100 |
| Untreated | 0 | 0 | 0 | 0 | 0 | 0 | 5 |

A is bifenthrin
B is clothianidin

Example 3

Test to Determine Termite Mortality by Applications of Combinations of Bifenthrin and Thiamethoxam The compositions of the present invention were tested for termiticide activity in the following manner:

Test compositions made up of TALSTAR® TERMITICIDE/INSECTICIDE and a wettable powder of thiamethoxam in distilled water were prepared that provided appropriate rates of application of combinations of bifenthrin and thiamethoxam, as well as bifenthrin and thiamethoxam alone.

Glass tubing, 13 mm in diameter, was then cut into 20 cm sections in sufficient quantity to conduct the test. Each 20 mm section of tubing was marked at 5 cm, 8 cm, and 18 cm distances from one end of the tube designated as the bottom. Each section of tubing was packed with a sandy soil (3% wt/wt moisture content) by first placing a section of a 1 cm diameter wooden dowel into the bottom of the glass tube up to the 8 cm marking, then introducing approximately 2 cm of soil into the other end of the tube designated as the top. The soil was then gently packed into the tube from the top using a second section of the 1 cm diameter wooden dowel. The process was repeated using 2 cm aliquots of soil until the soil level was adjacent to the 18 cm marking, thereby providing a column of soil 10 cm in height. An agar plug, which was formed in a section of the 13 mm diameter glass tubing of the type used to conduct these tests, was cut into 3 cm sections. A 3 cm section of agar was then gently pushed into the bottom of each tube containing the soil until the agar plug firmly touched the soil at the 8 cm marking, thereby creating a 5 cm void in the bottom of each section of tubing. Following placement of the agar plugs in each section of tubing; two sections of applicator sticks cut in 6 cm lengths were inserted into the bottom end of each tube thereby forcing about 1 cm of each stick into the agar plug to hold the agar plug in place. Plastic caps, with an inside diameter of 13 mm and holes drilled in their centers, were placed on the bottom ends of each of the sections of tubing. A sharpened applicator stick was then inserted into the hole in each plastic cap through the agar plug to the intersection of the agar plug and the soil. The applicator stick was then gently removed in a rotating manner to provide a means for a free flow of liquid through the soil. Each section of tubing was then stood upright, and 0.5 mL aliquots of each suspension of bifenthrin, thiamethoxam or combinations thereof, as prepared above, were pipetted onto the top of the soil. Upon application of the test suspensions the top of each section of tubing was covered with a small piece of aluminum foil. The tubes were then allowed to stand for about 20 hours to allow movement of the termiticide(s) downward into the soil. After this time a plastic cap of 13 mm inside diameter was placed on the top of each section of tubing. The plastic caps with the holes drilled in their centers were removed from the bottom of each section of tubing, and a piece of 0.5 cm×4 cm filter paper was then placed between the two sections of applicator sticks. Fifty termite (*Reticulitermes flavipes*) workers were then inserted into the 5 cm void in the bottom of each section of tubing. New plastic caps without holes drilled in their centers were placed on the bottom of each section of tubing. The sections of tubing were then stored in an upright position, with the termites located below the soil. Termite mortality was measured at 1 hour, 2 hours, 1 day, 2 days and 7 days after treatment. The following results were recorded:

TABLE 3

Control of Termites by Application of Combinations of Bifenthrin and Thiamethoxam

| Treatment | Rate of Appln. (PPM) | Rate of Appln. (% by weight) | Mortality Rate @ 1 Hour (%) | Mortality Rate @ 2 Hours (%) | Mortality Rate @ 1 Day (%) | Mortality Rate @ 2 Days (%) | Mortality Rate @ 7 Days (%) |
|---|---|---|---|---|---|---|---|
| A | 10 | 0.001 | 0 | 0 | 3 | 5 | 100 |
|  | 50 | 0.005 | 0 | 0 | 10 | 65 | 100 |
| B | 100 | 0.01 | 0 | 0 | 0 | 4 | 100 |
|  | 200 | 0.02 | 0 | 0 | 1 | 20 | 100 |
| A + B | 10/100 | 0.001/0.01 | 0 | 0 | 21 | 68 | 100 |
|  | 10/200 | 0.001/0.02 | 0 | 0 | 20 | 83 | 100 |
|  | 50/100 | 0.005/0.01 | 0 | 0 | 21 | 84 | 100 |
|  | 50/200 | 0.005/0.02 | 0 | 0 | 9 | 80 | 100 |
| Untreated | 0 | 0 | 0 | 0 | 0 | 1 | 1 |

A is bifenthrin
B is thiamethoxam

In the context of the present invention, the term "termiticide" refers to the active chemical compound or ingredient, such as bifenthrin, imidacloprid, nithiazinc, thiamethoxam, dinotefuran, nitenpyram, thiacloprid or clothianadin that kills or repels termites. The term "liquid termiticide" refers to a composition of a termiticide where the composition can be dispensed in an aqueous medium prior to its application to a locus where termite control is desired. The term "locus" refers to any locations where control of termites is needed or is expected to be needed. Such locations include, without limitation, buildings, trees, posts poles, fences, and locations adjacent to buildings, trees, posts poles, fences, as well as other locations. The term "repellency" refers to driving back, warding off, or keeping termites away through the use of a termiticide in a termite barrier. The terms "mortality", "percent mortality", "control", or "percent control" may be used interchangeably, and refer to the killing of and/or repelling of termites.

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. A method for controlling termites comprising applying a termiticidally effective amount of a termite composition dispersed in an aqueous medium wherein the termiticide consists of a mixture of
   (i) bifenthrin and
   (ii) clothianadin,
wherein the amount of bifenthrin is equal to from 0.0005% by weight to 0.50% by weight of all components in the composition and the amount of clothianadin is equal to from 0.0005% by weight to 0.50% by weight of all components in the composition to a locus where termite control is needed or expected to be needed, wherein said locus is selected from a termite-infested structure, a structure that is expected to be termite-infested, or a location adjacent to said structures.

2. The method of claim 1 wherein the weight ratio of bifenthrin:clothianadin is between 1:2 and 1:20.

3. The method of claim 1 wherein the amount of bifenthrin is equal to from 0.001% by weight to 0.005% by weight of all components in the composition and the amount of clothianadin is equal to from 0.01% by weight to 0.02% by weight of all components in the composition.

4. The method of claim 1 wherein such termites are of the species *Reticulitermes flavipes*.

* * * * *